United States Patent
Charles

(10) Patent No.: US 10,034,796 B2
(45) Date of Patent: Jul. 31, 2018

(54) SEMI-AUTOMATED OPHTHALMIC PHOTOCOAGULATION METHOD AND APPARATUS

(71) Applicant: TOPCON MEDICAL LASER SYSTEMS, INC., Santa Clara, CA (US)

(72) Inventor: Steven Thomas Charles, Memphis, TN (US)

(73) Assignee: TOPCON MEDICAL LASER SYSTEMS INC., Santa Clara, CA (US)

( * ) Notice: Subject to any disclaimer, the term of this patent is extended or adjusted under 35 U.S.C. 154(b) by 834 days.

(21) Appl. No.: 14/095,523

(22) Filed: Dec. 3, 2013

(65) Prior Publication Data

US 2014/0094784 A1 Apr. 3, 2014

Related U.S. Application Data

(62) Division of application No. 11/868,387, filed on Oct. 5, 2007.

(51) Int. Cl.
*A61F 9/008* (2006.01)
*A61F 9/007* (2006.01)
(Continued)

(52) U.S. Cl.
CPC .......... *A61F 9/00823* (2013.01); *A61B 3/102* (2013.01); *A61B 3/135* (2013.01);
(Continued)

(58) Field of Classification Search
CPC ................ A61F 9/0008; A61F 9/00821; A61F 9/00823; A61F 9/0079; A61F 2009/00846;
(Continued)

(56) References Cited

U.S. PATENT DOCUMENTS

| 4,641,349 A | 2/1987 | Flom et al. |
| 4,917,486 A | 4/1990 | Raven et al. |

(Continued)

FOREIGN PATENT DOCUMENTS

| CN | 1379647 A | 11/2002 |
| CN | 1433287 A | 7/2003 |

(Continued)

OTHER PUBLICATIONS

JP2014-248554 Office action dated Oct. 27, 2015.
(Continued)

*Primary Examiner* — Paula J Stice
(74) *Attorney, Agent, or Firm* — Pearne & Gordon LLP

(57) ABSTRACT

An ophthalmic treatment system of an embodiment is used for performing therapy on target tissue in a patient's eye. The ophthalmic treatment system comprises, a light source, a delivery system, an obtaining means, a setting means and control electronics. The light source is configured to produce treatment light. The delivery system is configured to deliver the treatment light to the patient's eye. The obtaining means is configured to obtain information acquired by capturing the patient's eye. The setting means is used for setting a position in the patient's eye by using the information obtained by the obtaining means. The control electronics is configured to control the delivery system based on the position set by the setting means.

5 Claims, 5 Drawing Sheets

(51) Int. Cl.
*A61B 3/10* (2006.01)
*A61B 3/135* (2006.01)

(52) U.S. Cl.
CPC ............ *A61F 9/008* (2013.01); *A61F 9/0079* (2013.01); *A61F 9/00821* (2013.01); *A61F 2009/00846* (2013.01); *A61F 2009/00851* (2013.01); *A61F 2009/00863* (2013.01); *A61F 2009/00878* (2013.01); *A61F 2009/00897* (2013.01)

(58) Field of Classification Search
CPC .... A61F 2009/2009; A61F 2009/00863; A61F 2009/00878; A61F 2009/00897
USPC .......................................................... 606/4
See application file for complete search history.

(56) References Cited

U.S. PATENT DOCUMENTS

| | | | |
|---|---|---|---|
| 5,029,220 | A | 7/1991 | Juday |
| 5,098,426 | A | 3/1992 | Sklar et al. |
| 5,179,421 | A | 1/1993 | Parker et al. |
| 5,391,165 | A | 2/1995 | Fountain et al. |
| 5,865,832 | A | 2/1999 | Knopp et al. |
| 6,099,522 | A | 8/2000 | Knopp et al. |
| 6,179,421 | B1 | 1/2001 | Pang |
| 6,312,423 | B1 | 11/2001 | Ota et al. |
| 6,702,809 | B1 | 3/2004 | Knopp et al. |
| 6,726,680 | B1 | 4/2004 | Knopp et al. |
| 6,733,490 | B1 | 5/2004 | Falsini et al. |
| 7,044,602 | B2 | 5/2006 | Chernyak |
| 7,146,983 | B1 | 12/2006 | Hohla et al. |
| 7,452,081 | B2 * | 11/2008 | Wiltberger ........... A61B 3/0091 351/211 |
| 7,635,186 | B2 | 12/2009 | Kobayashi et al. |
| 7,768,652 | B2 | 8/2010 | Everett |
| 8,336,555 | B2 | 12/2012 | Palanker |
| 8,734,433 | B2 | 5/2014 | Palanker |
| 9,387,123 | B2 | 7/2016 | Palanker |
| 9,498,295 | B2 | 11/2016 | Palanker |
| 9,681,985 | B2 | 6/2017 | Andersen |
| 2002/0007177 | A1 | 1/2002 | Campin et al. |
| 2002/0151877 | A1 | 10/2002 | Mason |
| 2002/0173778 | A1 | 11/2002 | Knopp et al. |
| 2002/0198516 | A1 | 12/2002 | Knopp et al. |
| 2003/0144651 | A1 | 7/2003 | Teiwes et al. |
| 2003/0223037 | A1 | 12/2003 | Chernyak |
| 2004/0059321 | A1 | 3/2004 | Knopp et al. |
| 2004/0143244 | A1 * | 7/2004 | Gray .................. A61B 3/15 606/5 |
| 2005/0024586 | A1 | 2/2005 | Teiwes et al. |
| 2005/0270486 | A1 | 12/2005 | Teiwes et al. |
| 2005/0273185 | A1 | 12/2005 | Teiwes et al. |
| 2005/0286019 | A1 | 12/2005 | Wiltberger et al. |
| 2005/0288745 | A1 * | 12/2005 | Andersen ............ A61F 9/00781 607/86 |
| 2006/0100677 | A1 | 5/2006 | Blumenkranz et al. |
| 2007/0055222 | A1 | 3/2007 | Hohla et al. |
| 2007/0121069 | A1 | 5/2007 | Anderson et al. |
| 2007/0126985 | A1 | 6/2007 | Wiltberger et al. |
| 2007/0129775 | A1 | 6/2007 | Mordaunt et al. |
| 2007/0171369 | A1 | 7/2007 | Grundig |
| 2008/0015553 | A1 | 1/2008 | Zacharias |
| 2008/0300581 | A1 | 4/2008 | Wiechmann et al. |
| 2009/0093798 | A1 | 4/2009 | Charles |
| 2010/0249760 | A1 | 9/2010 | Blumenkranz et al. |
| 2010/0256615 | A1 | 10/2010 | Blumenkranz et al. |
| 2013/0304046 | A1 | 11/2013 | Charles |
| 2013/0345683 | A1 | 12/2013 | Mordaunt et al. |
| 2014/0081248 | A1 | 3/2014 | Blumenkranz et al. |
| 2014/0094784 | A1 | 4/2014 | Charles |
| 2014/0094785 | A1 | 4/2014 | Charles |
| 2015/0100049 | A1 | 4/2015 | Mordaunt et al. |
| 2015/0173952 | A1 | 6/2015 | Nomura |
| 2015/0202083 | A1 | 7/2015 | Takeda |
| 2015/0265465 | A1 | 9/2015 | Charles |
| 2016/0287441 | A1 | 10/2016 | Palanker |

FOREIGN PATENT DOCUMENTS

| | | | |
|---|---|---|---|
| DE | 10 2005 055 885 A1 | | 5/2007 |
| JP | 4-166149 A | | 6/1992 |
| JP | 3095079 B2 | | 8/2000 |
| JP | 2000-513965 A | | 10/2000 |
| JP | 2000513965 A | | 10/2000 |
| JP | 2000342620 A | | 12/2000 |
| JP | 2004524052 A | | 8/2004 |
| JP | 2005528600 A | | 9/2005 |
| JP | 2006524515 A | | 11/2006 |
| JP | 2008504075 A | | 2/2008 |
| JP | 2008521508 A | | 6/2008 |
| JP | 2011-501985 A | | 1/2011 |
| JP | 2011501985 A | | 1/2011 |
| WO | 1987/005205 A1 | | 9/1987 |
| WO | 1993/016631 A1 | | 9/1993 |
| WO | 1998/000078 A1 | | 1/1998 |
| WO | 199800078 A1 | | 8/1998 |
| WO | 2001/028476 A1 | | 4/2001 |
| WO | 2001/047426 A1 | | 7/2001 |
| WO | 2006005038 A2 | | 1/2006 |
| WO | 2006/060323 A1 | | 6/2006 |
| WO | 2007035855 A2 | | 3/2007 |
| WO | 2007059189 A1 | | 5/2007 |
| WO | 2008/033933 A1 | | 3/2008 |

OTHER PUBLICATIONS

Office action for U.S. Appl. No. 14/095,600 dated Aug. 17, 2016.
Extended European Search Report and European Search Opinion received for European Patent Application No. 08835609.2, dated Feb. 28, 2012, 7 pages.
Office Action received for Chinese Patent Application No. 200880110156.8, dated May 31, 2011, 19 pages (12 pages of English Translation and 7 pages of Office Action).
International Search Report and Written Opinion received for PCT Patent Application No. PCT/US2008/010984, dated Dec. 8, 2008, 6 pages.
International Preliminary Report on Patentability received for PCT Patent Application No. PCT/US2008/010984, dated Apr. 7, 2010, 6 pages.
Office action dated Jul. 5, 2016 for Japanese Application No. 2015-183626.
Office action dated Jul. 12, 2016 for Japanese Application No. 2015-172476.
Office action dated Aug. 2, 2016 for Japanese Patent Application No. 2015-201795.
Office Action for JP2013-231931 dated Sep. 16, 2014.
Office Action for JP2015-183626 dated Dec. 27, 2016.
Office Action received for Indian Patent Application No. 2494/CHENP/2010, dated Nov. 30, 2016, 7 pages.
Office Action received for Japanese Patent Application No. 2010-527943, dated May 8, 2013, 8 pages (3 pages of English translation and 5 pages of Official Copy).
Office Action Received for Japanese Patent Application No. 2010-527943, dated Jul. 5, 2012, 6 pages (3 pages of English Translation and 3 pages of Official Copy).
Office Action received for Japanese Patent Application No. 2010-527943, dated Jul. 23, 2014, 3 pages of official copy only. (See communication under 37 CFR § 1.98(a) (3)).
Response to Office Action for U.S. Appl. No. 13/944,436 dated Sep. 26, 2017.
Markow, M.S., et al., "An Automated Laser System for Eye Surgery", IEEE Engineering In Medicine and Biology Magazine, Dec. 1989, pp. 24-29, Los Angeles, California.

* cited by examiner

SEMI-AUTOMATED OPHTHALMIC PHOTOCOAGULATION METHOD AND APPARATUS

RELATED APPLICATION

This application is a divisional of U.S. patent application Ser. No. 11/868,387 filed on Oct. 5, 2007, which is incorporated herein by reference in its entirety.

FIELD OF THE INVENTION

The present invention pertains generally to the ophthalmic treatment of a patient's eye, and more particularly to a machine and method for semi-automated ophthalmic photomedical treatment of a patient's eye.

BACKGROUND OF THE INVENTION

Presently, conditions such as diabetic retinopathy, vein occlusion and age-related macular degeneration have been treated with photocoagulation induced by visible laser light. While this type of visible laser light treatment may halt the progress of the underlying disease, it can be problematic.

One problem is that some ophthalmic treatments require the application of a large number of laser doses to the retina, which can be tedious and time consuming. Such treatments call for the application of each dose in the form of a laser beam spot applied to the target tissue for a predetermined amount of time. The physician is responsible for ensuring that each laser beam spot is properly positioned on the intended target tissue as well as away from sensitive areas of the eye such as the macula that could result in permanent unintended damage. Since some treatments can require hundreds of laser beam spots to treat the target tissues, the overall treatment time can be quite long and require great physician skill to ensure a precise and adequate treatment of the entire target tissue area is accomplished.

To reduce the treatment time needed for retinal photocoagulation, a system and method has been proposed for applying multiple laser spots automatically in the form of a treatment pattern of spots, so that an area of target tissue is efficiently treated by multiple spots pre-positioned on the tissue in the form of the pattern. See for example U.S. Patent Publications 2005/0286019, 2006/0100677 and 2007/0129775. However, rapid delivery of multiple beam spots in patterns raises new issues. For example, the exposure time is limited because of possible eye movement, and even with short exposure times there can be patient eye movement at the moment the physician triggers the application of the treatment pattern that could result in the application of the treatment pattern to non-targeted tissue. Moreover, physicians typically identify the tissue locations to be targeted using pre-treatment images of the eye. Present systems and techniques for applying patterns of spots have no capability of ensuring the tissue targeted for treatment by the physician is the same as that identified in the pre-treatment images. Thus, the physician is solely responsible for ensuring the tissue about to be treated is the same tissue identified in the pre-treatment images, and that the stability of the eye position will allow an accurate application of the treatment pattern. Rapid eye movements called saccades cannot be adequately tracked or compensated for by physicians. Typical physician latency times are approximately 400 ms, and thus physicians usually can only move the laser aiming device at a 5 Hz rate (while eye movements are approximately 100 times faster). Anesthetizing eye muscles using an injection of an anesthetic agent behind the eye can stabilize the eye but carries a risk of perforating the eye, the optic nerve or the blood vessels, is quite painful, and could even cause death.

Accordingly, there is a need for a semi-automated ophthalmic laser treatment and method that compensates for patient eye movement, and/or can assist the physician in verifying and adjusting alignment of the treatment pattern to the target tissue identified in pre-treatment images of the eye.

SUMMARY OF THE INVENTION

An embodiment solves the aforementioned problems by providing an ophthalmic treatment system for performing therapy on target tissue in a patient's eye, comprising: a light source configured to produce treatment light; a delivery system configured to deliver the treatment light to the patient's eye; an obtaining means configured to obtain information acquired by capturing the patient's eye; a setting means that is used for setting a position in the patient's eye by using the information obtained by the obtaining means; and control electronics configured to control the delivery system based on the position set by the setting means.

Other objects and features of the present invention will become apparent by a review of the specification, claims and appended figures.

DETAILED DESCRIPTION OF THE PREFERRED EMBODIMENTS

A system and method for semi-automated, doctor-in-the-loop, ophthalmic treatment of target eye tissue is disclosed which accurately identifies tissue areas for treatment, aligns a light delivery system to those tissue areas for treatment, and adjusts alignment to compensate for patient eye movement during treatment.

Pattern Generation System

Figure 1:
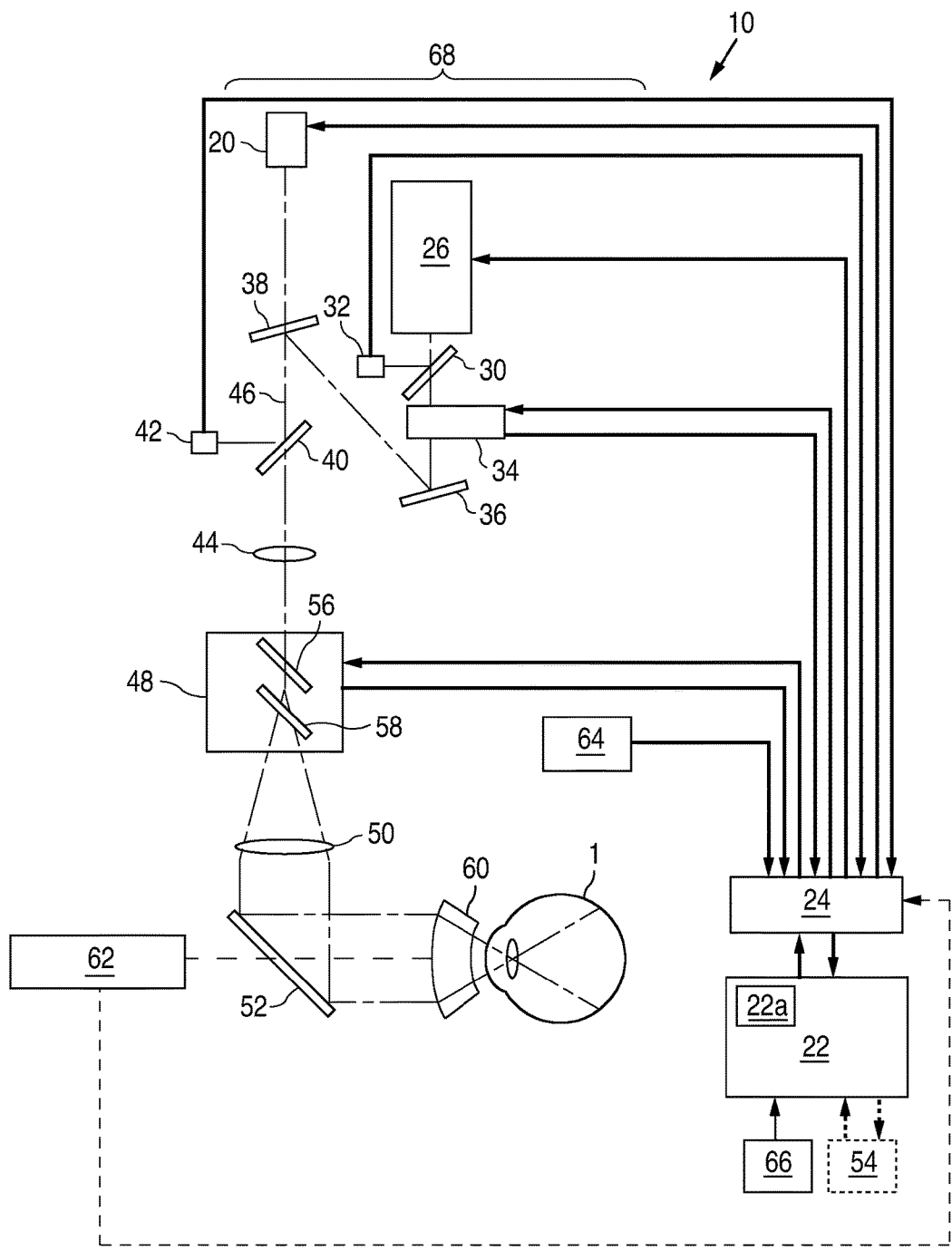
FIG. 1 is a schematic diagram illustrating a light generation and scanner system for semi-automated ophthalmic treatment.
Figure 2A:
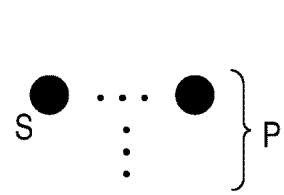
FIGS. 2A-2D illustrate exemplary scan patterns for use with a pulsed or gated light source.
Figure 2B:
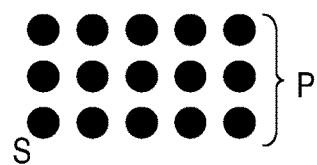

FIG. 1 is a schematic diagram of a system 10 suitable for performing semi-automated ophthalmic treatment of a patient's eye tissue. Alignment light (for an aiming beam or alignment pattern) is created using an alignment light source 20, which may be controlled by control electronics 22 via an input/output device 24. It should be noted that the use of alignment light is optional, and therefore elements for its generation and use could be omitted. Therapeutic light is created using a therapeutic light source 26. Light sources 20 and 26 can be any gas or solid state laser device, or even one or more light emitting diodes. Light sources 20/26 are preferably separate devices because they typically will produce light at different wavelengths and power levels. However, they could be combined into a single light source that produces light at different alignment and therapeutic light with differing or identical wavelengths. Alignment light from source 20 preferably is visible to the eye (however, if an alternate visualization scheme such as infrared imaging is employed, it may be non-visible). Therapeutic light from source 26 may also be visible, but need not be. If therapeutic light source 26 does produce visible light, it may be also used for producing the alignment light instead of alignment light source 20 (e.g. by simply reducing its output power during system alignment when no eye safety filters are in the visualization pathway). Likewise, if therapeutic light source 26 produces non-visible light, it may be used for alignment in a similar manner with a non-visible imaging scheme (e.g. by using an infrared imaging device).

Light output from therapeutic light source 26 first encounters a mirror 30 which reflects a fixed portion of the therapeutic light to a photodiode 32 to measure its power for safety and real time power adjustment purposes. The therapeutic light then encounters shutter 34, mirror 36, and mirror 38. Shutter 34 fundamentally serves to control the delivery of the therapeutic light, and can be used to rapidly gate and/or generally block the therapeutic light. Mirror 36 is an optional turning mirror, and mirror 38 is used to combine the therapeutic light with the alignment light from light source 20 to form combined alignment/therapeutic light beam 46, where alignment light from source 20 may be adjusted so that it is coincident with the therapeutic light downstream. It should be noted that the alignment light and the therapeutic light would typically not be produced simultaneously, and in that case mirror 36 in actuality combines beam paths for these two beams of light (i.e. alignment/therapeutic light 46 contains only alignment light at certain times and therapeutic light at other times). A mirror 40 is used to reflect a portion of the combined alignment and therapeutic light into photodiode 42 for additional measurement (and also provides redundant monitoring of the state of shutter 34).

A lens 44 can be used to focus the combined alignment/therapeutic light 46 prior to its entry into a scanner assembly 48. Lens 44 may be a single lens, or a compound lens. If lens 44 is a compound lens, it may be configured as a zoom lens assembly that adjusts the size of spots S, and therefore, pattern P. Another lens 50 can be placed one focal length away from the optical midpoint of the scanner assembly 48 to produce a telecentric scan (however this is optional). For systems including lens 50, a telecentric scan serves to maximize the scan speed, so long as the remaining optical elements are large enough to contain the entire scan. Most of the current available optical treatment contact lenses demand telecentric input.

Scanning assembly 48 preferably includes two optical elements 56 and 58 (e.g. mirrors, lenses, diffractive elements, rotating wedges, etc.), that can be individually tilted or moved in an orthogonal manner to deviate (deflect) the optical beam 46, and ultimately direct it towards the target tissue in the form of a pattern P (such as those shown in FIGS. 2A-2D and 3a-3D, and described in further detail below). For example, optical elements 56/58 can be mirrors mounted to galvanometers, solenoids, piezoelectric actuators, motors, servos, motors or other type of actuators for deflecting the beam 46 by tilting the mirrors. Of course, single element 2-dimensional scanners may also be used, such as acousto-optic deflectors, optical phased arrays, or micro mirror devices. Alternately, the mirrors could have optical power (e.g. have surface curvature), where deflecting the beam can be accomplished by translating the mirrors. Or, optical elements 56/58 could be one or more lenses, which deflect the beam by translational movement of the lenses.

Light 46 next encounters mirror 52, which reflects the light toward the target tissue in the patient's eye 1. Mirror 52 includes a high reflective coating that spectrally matches the outputs of the alignment and therapeutic light, yet allows visualization light coming from the target to pass through so that target area can be visualized through mirror 52. Preferably, the coating would be constructed to white balance the transmission through mirror 52, where the coating is more complicated and makes the colors appear more natural instead of a pinkish result when using a green notch filter coating. Lens 50 may also be used to image the optical midpoint of the scanner assembly 48 onto mirror 52, to minimize the size of the mirror 52 in an attempt to increase the overall solid angle subtended by the visualization device. When mirror 52 is small, it may be placed directly in the visualization path without much disturbance. Mirror 52 may also be placed in the center of a binocular imaging apparatus, such as a Zeiss slitlamp biomicroscope, without disturbing the visualization.

An optional ophthalmic lens 60 may be placed directly before the eye to aid in visualization, such as might be done with any ophthalmoscope, slit lamp biomicroscope, fundus camera, SLO, or OCT system. Ophthalmic lens 60 may be a contact or non-contact lens, and may also be used in conjunction with lens 50 to provide for conjugate pupil planes such that the scanning pivots about the patient's iris, thus maximizing the system's retinal scan field. Visualization of the target tissue is preferably accomplished by directly viewing the retina through mirror 52 by the physician (e.g. using a slitlamp biomicroscope) as well as using a high frame rate camera 62 (e.g. CCD or CMOS camera) to create an electronic image from the light passing through mirror 52. The electronic image can be stored by the system, displayed on a graphical user interface (GUI) 54, and used by the control electronics 22 to confirm/adjust alignment as described below.

The mirrors, lenses and other optical elements between the light sources 20/26 and the patient's eye 1 form a delivery system 68 that can be controlled to deliver the alignment/treatment patterns to the intended target tissue. More specifically, scanner 48, under the control the control electronics 22, creates the alignment and treatment patterns P of the alignment and therapeutic light respectively, as discussed in further detail below with respect to FIGS. 2A-2D and 3A-3D. Any other components of delivery system 68 can be movably controlled by control electronics 22, and thus affect the final alignment of delivery system 68. The position and character of pattern P may be manually controlled by the physician adjusting the position of lens 60, as well as electronically controlled by commands or controls input via a graphic user interface (GUI) 54 and/or automated control by the control electronics 22 as described below. GUI 54 can be a single touch screen for displaying system options, entering commands, and viewing images from camera 62 as well as imported images. Alternately, GUI 54 can comprise several separate components, including a keypad or keyboard for entering commands, a touch sensitive screen for viewing system options and entering system commands, and/or a stand alone visual display screen for viewing images from camera 62 (as well as viewing pre-treatment images and treatment templates described in more detail below). Pattern P, or any of its elements, may also be made to be perceived by the physician as blinking.

Alignment/Treatment Patterns

The alignment and treatment patterns generated by system 10 may be comprised of a single spot of light, multiple spots of light, a continuous pattern of light, multiple continuous patterns of light, and/or any combination of these, utilizing either or both continuous wave (CW) and pulsed light sources, for standard, selective, and/or sub-threshold therapies (i.e. therapies that do not result in any visible signs of treatment). In addition, the alignment pattern need not be identical to the treatment pattern, but preferably defines its location (e.g. its boundaries or its center, etc.) in order to assure that the therapeutic light is delivered only within the desired target area or at a location centered at a particular location. This may be done, for example, by having the alignment pattern provide an outline of the intended treatment pattern, or a point or cross-hairs showing a center position. This way, the spatial extent or center point of the treatment pattern may be made known to the physician, if not the exact locations of the individual spots themselves, and the scanning thus optimized for speed, efficiency and accuracy.

Figure 3A:
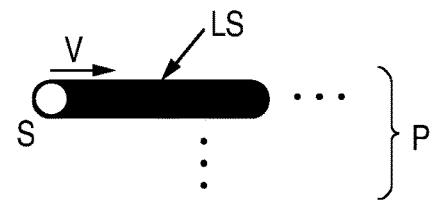
FIGS. 3A-3D illustrate exemplary scan patterns for use with a continuous wave (CW) light source.
Figure 3B:
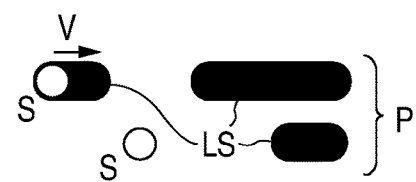
Figure 2C:
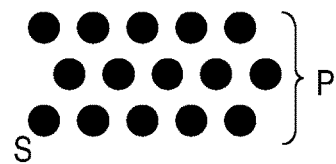
Figure 3C:
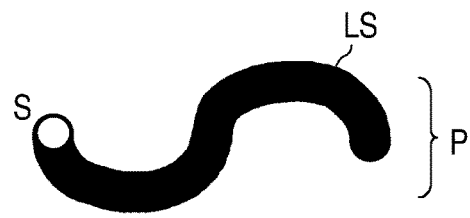
Figure 2D:
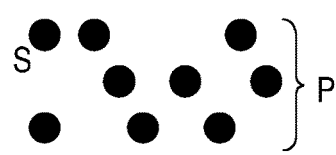
Figure 3D:
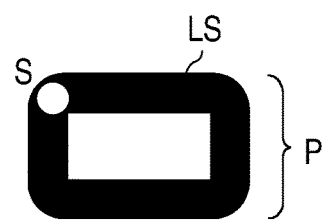

The alignment and treatment patterns are preferably formed as a pattern P of spots S of light projected onto the target tissue, as illustrated in FIGS. 2A-2D. Spots S are shown as round, but need not be. FIGS. 3A-3D illustrate how one or more spots S can be used to trace out or even form elongated straight or curved line segments to form patterns P, which is ideal for continuous wave (CW) light sources. For example, in FIG. 3A, spot S is scanned at a velocity V to form line segment scans LS of pattern P. Each line segment LS terminates when the light source is no longer delivering light to the spot S being scanned that forms the line segment LS. This may be done in many ways, such as, gating the light source on-and-off directly, using a shutter placed in the optical path, by use of an aperture, etc. As shown in FIG. 3B, a pattern P may be formed of a plurality of line segments LS and/or spots S. The line segment LS may be shaped or curved, as illustrated in FIG. 3C, or even curved/shaped to form geometric objects or symbols as illustrated in FIG. 3D (which is particularly suited as an outline of the target tissue for the alignment pattern as previously discussed).

Thus, for the purposes of this disclosure, a "pattern" of light shall mean at least two spots S that do not completely overlap (or do not overlap at all), or one or more spots that move during a single pulse or with CW light resulting in a projected straight or curved line segment. Additionally, the alignment pattern need not be identical to the treatment pattern. For example, if a treatment pattern contains hundreds of spots, its location can be identified by less complicated indicia (e.g. alignment pattern of just a few spots showing boundaries and/or the center of the treatment pattern). In fact, a single stationary alignment beam spot showing the center of the treatment pattern could be used. Simplified alignment patterns, or use of a single stationary alignment beam spot, can be projected more simply and quickly than trying to replicate the entire treatment pattern with the alignment light.

Semi-Automated Alignment Confirmation and Compensation

Typically, physicians use one or more pre-treatment images and/or two dimensional or three dimensional data sets of the patient's eye (images of the eye often taken well before the treatment—sometimes earlier by days and at a different clinical location using different equipment) to identify the precise locations of tissue to be targeted for treatment. During conventional treatment procedures, the physician must manually identify and target the patient's eye tissue that was previously identified using the pre-treatment images. If there is any mismatch between the tissue locations previously identified in the pre-treatment images and those targeted during treatment, then healthy tissue will end up being treated and intended target tissue will escape treatment. Therefore, to better compliment the physician's alignment of treatment pattern to the intended target tissue, the system 10 uses one or more pre-treatment images to produce a treatment template which is registered to a live image of the patient's eye to verify alignment, compensate for patient eye movement, and/or control varying dosages of treatment light even within the same treatment pattern.

Figure 4:
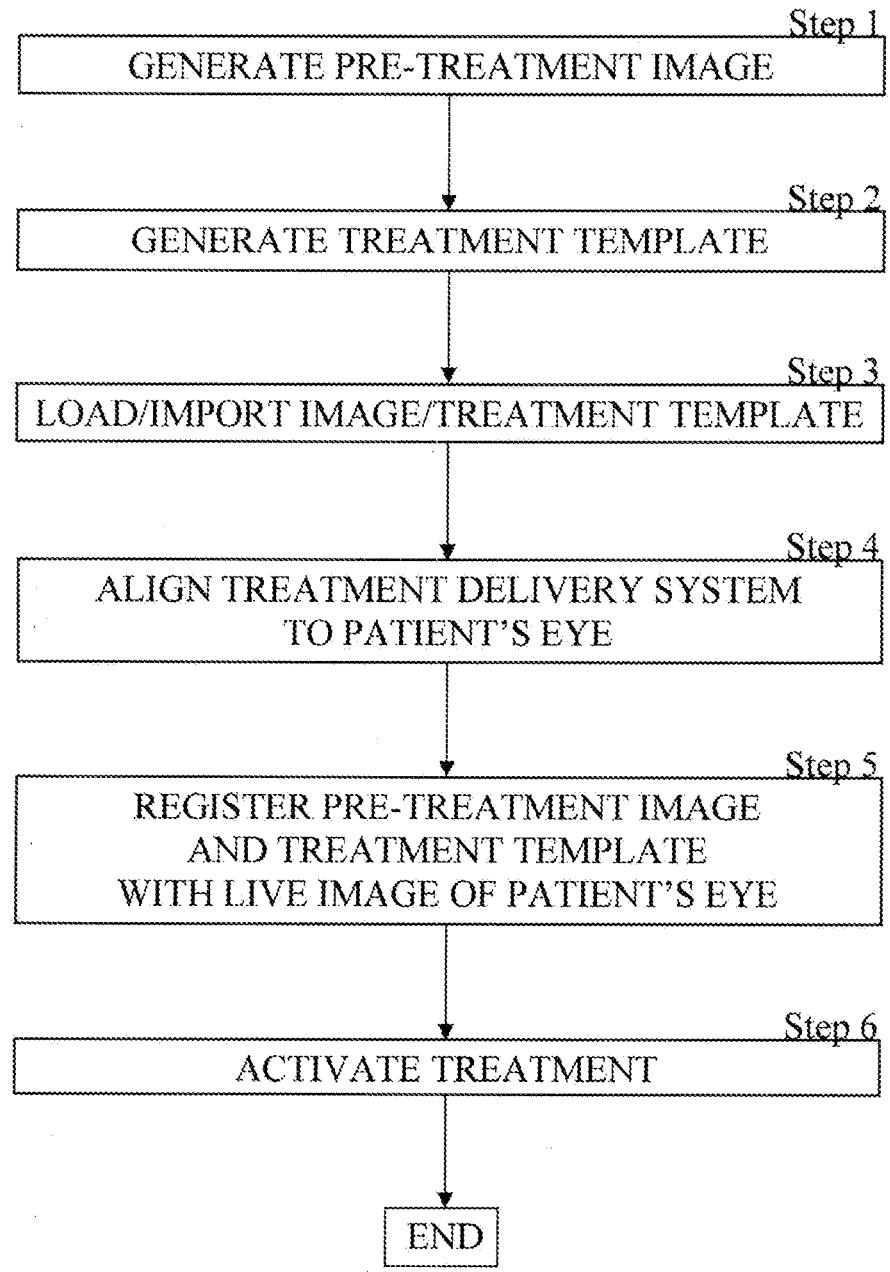
FIG. 4 is a flow diagram illustrating a method of semi-automated ophthalmic treatment.

FIG. 4 illustrates the method of semi-automated alignment confirmation and compensation. In step 1, a pre-treatment image of the eye is generated. While the following discussion refers to a single pre-treatment image for simplicity, multiple pre-treatment images of the same or different type can be generated as well. Image generation can be performed immediately before treatment at the treatment site, or at a different location long before treatment. Sources of the pre-treatment image can include a digital color fundus camera image, a fundus camera angiogram, a confocal angiogram, a wide-field angiogram (recent emphasis on peripheral ischemia in diabetic retinopathy), an indocyanine green angiogram, an auto-fluorescence image, a monochromatic image, an infrared image, a spectral domain or time domain 3D OCT (ocular coherence tomography) with point-to-point registration to fundus (retinal) image, a multi-focal ERG, a preferential hyperacuity perimetry, or a static perimetry data set. The data forming the pre-treatment image can be 2D or 3D mapped functional data, OCT data, etc. The image can also be a composite image using multiple different sources of 2D data and images from the patient's eye.

In step 2, a treatment template is created which identifies what portion(s) of the tissue in the pre-treatment image should be treated. The treatment template is preferably constructed using an electronic computing device with a visual display and user inputs such as a joystick, mouse or other pointing device. This computing device could be separate from the treatment system, or can be integral to the treatment system. For example, the treatment template can be formed by loading the pre-treatment image into a conventional computer, and then digitally marking locations in that image which warrant treatment using the computer's display screen and conventional computer input devices (keyboard, mouse, joystick, touchscreen, etc.). Alternately, the pre-treatment image can be loaded into system 10 using an input port 66, where the computing device includes control electronics 22. The treatment template can then be generated using the GUI 54 and possibly one or more input devices 64.

Preferably, the computing device for creating the treatment template includes software or hardware tools for aiding the physician in marking locations on the image of the patient's eye for treatment. For example, the computing device can include tools for adding or subtracting spots from a treatment pattern, or allow the physician to outline an area for treatment in which a treatment pattern is added. Ideally the computing device will aid the physician in determining one or more treatment patterns for which the system 10 described above is capable of producing. The computing device could provide a library of sample treatment patterns of adjustable size and shape, to allow the physician to select, locate and adjust one or more treatment patterns to cover entire areas of the image for which treatment is warranted. Typical patterns could include but are not be limited to:

initial or fill-in pan retinal photocoagulation (PRP), grid treatment pattern, sector treatment pattern, patterns that "paint" a choroidal neovascular membrane, patterns that "paint" around a retinal hole or tear, or patterns that "paint" around automatically identified areas for treatment of microaneurysms, patterns required by a clinical trial, and/or custom patterns developed by an expert or frequent user. In developing treatment patterns, the computing device can be configured to automatically build treatment patterns that avoid certain areas of the image. For example, the computing device can be set to locate and avoid shapes or areas that are black (indicating previous treatment) or red (indicating large vessels or blood), or avoid physician designated areas such as the fovea and optic nerve. The computing device can also be configured to locate and target areas that are likely targets, such as a choroidal neovascular membrane, microaneurysms, or a central serous retinopathy leak. Spot size could vary by location. PRP spots could be larger in the periphery and smaller near the posterior pole, and could be evenly interspersed between previous spots determined by the black avoidance algorithm described above or a registered template from a previous treatment session.

Treatment template generation need not be limited to identifying and controlling just treatment locations. Dosage control information can also be embedded into the treatment template, and used by the system 10 to automatically vary the dosage (power, spot size and duration) of treatment light for various locations within the targeted tissue. This can be an automated function performed by the computing device, or manually performed by the physician, or a combination of the both. For example, laser energy absorption is generally a function of pigmentation. Tissues that are lighter in color or are more reflective will generally require a higher dosage of treatment light. In contrast, tissues that are dark are more absorptive, and will generally require a lower dosage of treatment light. In generating the treatment template, pigmentation and reflectance/absorption characteristics can be used by the computing device and/or the physician to determine the proper dosage for each spot or location within the targeted tissue. By including this information in the treatment template, the system 10 can then use this information to automatically adjust the laser power, and/or dwell time to provide the optimal treatment dosage at each location within the targeted tissue (even on a real time spot-by-spot basis for a treatment pattern containing hundreds of spots). Although the absorption measurement would be optimal if determined at a wavelength near the intended treatment wavelength, melanin is a broadband absorber, and rod and cone pigments are also cumulatively green absorbers (near the most widely used treatment wavelengths), which means that imaging at the exact treatment wavelength may not be needed for many procedures employing automated dosage control. Automated dosage control will result in producing greater accuracy and safety, enabling more precise sub-threshold treatment and reducing the likelihood of Bruch's membrane rupture and bleeding.

The treatment template represents a digital overlay for the pre-treatment image that defines locations and dosages of treatment, including the precise treatment pattern(s) and dosages within such treatment pattern(s). The treatment template can be incorporated into the same digital file containing the pre-treatment image, or typically stored as a separate digital file. Using a treatment template allows the physician to take his or her time to precisely define exactly where treatment spots or patterns will be applied, and at what dosages, by careful analysis of the pre-treatment image outside of the patient's presence (and possibly even outside of any clinical environment). The treatment template can even be "digitally signed" by the physician and indelibly archived for risk management purposes. The treatment template can also serve as an operation report after treatment.

In step 3, the pre-treatment image and treatment template are loaded into system 10 via input port 66, and preferably stored in a storage device 22a (e.g. hard drive, flash non-volatile memory, CD, DVD, etc.) that is contained within or connected to control electronics 22. Input port 66 can be a port for receiving electronic files from a storage device (i.e. CD/DVD disk, flash memory key, etc.), or a network connection for receiving electronic files over a network, or even provide a direct connection to the computing device used to generate the treatment template. If the system 10 is used to generate the treatment template, then this loading step would be omitted, as the pre-treatment image data would have been previously loaded into system 10, and the treatment template would have been created internally by system 10.

In step 4, the delivery system 68 is aligned to the patient's eye. This can be accomplished by the physician holding and aligning the lens 60 (preferably a contact lens) to the patient's eye (which solves image optimization, obliquity, reflections from the contact lens, pupil size, pupil decentration, corneal & lens opacities, and astigmatism problems), and/or by manipulating the alignment of the delivery system 68 via one or more input devices/controls 64 and/or GUI 54 while directly viewing the target tissue or using the real-time image from camera 62 as a guide. When the delivery system 68 is generally aligned to the patient's eye, camera 62 will capture a live image of the patient's eye, which is sent to control electronics 22 and displayed on GUI 54 or another display device.

In step 5, system 10 registers the pre-treatment image and treatment template to the live image from camera 66, so that the system 10 can precisely determine where on the pre-treatment image and treatment template the delivery system is presently aimed to. This image registration can be accomplished using affine transform or other stretching or morphing algorithms which match the two-dimensional video amplitudes of the live image from camera 62 to the two-dimensional video amplitudes of the pre-treatment image. This process involves stretching or morphing the pre-treatment image so as to create a best fit with the live image. Optionally, feature recognition techniques can be used to perform the image registration. As long as the alignment of the delivery system in step 4 is close to the intended target tissue (i.e. so there is substantial overlap between the pre-treatment and live images), the system 10 will recognize the live image and register the pre-treatment image to it.

Registration will likely not require megapixel images from camera 62, where resolutions as low as 512×512 or VGA (640/480) will likely prove to be sufficient (thus reducing cost and enabling higher frame rates and lower processing bandwidth than megapixel cameras). Camera 62 would typically include a monochromatic sensor with high fill factor (100%) to improve photon efficiency, or a progressively scanned sensor for better image processing. Camera 62 can include infrared or visible sensing which detects the retinal image from the white light illumination commonly used by physicians to illuminate and visualize the target tissue with the slitlamp biomicroscope. The frame rate of camera 62 should be significantly higher than video rates, as an unrestricted eye requires approximately 1 kHz for stabilization of saccadic movements. High viscosity coupling fluid and flanged lens contact with high surface area can be used to somewhat decrease saccadic velocities of the patient's eye.

It is desirable that the system maintain proper registration in the event of patient eye movement, meaning that the system 10 would preferably detect and track eye movement while maintaining registration. One non-limiting example of image registration that can track eye movement is to use pipeline processing (preferably using image processing on FPGA silicon such as done by Xilinix) implementing Chi square algorithms (which have been shown to be effective for retinal tracking). This process can be accomplished by comparing the two-dimensional video amplitude of the current frame of the live image of the patient's eye to that of the previous frame, to determine the directionality and amplitude of any movement. For example, the current frame image can be moved iteratively, for example, one pixel to the right, where a calculation is made to determine if there is a fit. This is repeated with movements left, up and down, until the best fit or match is achieved. Once the best fit is achieved, the amount of eye movement can be determined by how many XY pixel movements were needed to achieve the best fit/match. Those pixel movement adjustments are then applied to the treatment template positioning via movable mirrors to maintain proper registration with the live image.

It is preferable that the physician confirm that proper registration between the live camera image and the treatment template (built on the pretreatment image) has been achieved. This can be accomplished by using GUI 54, which can visually display an overlay of the live image and the treatment template. This overlay image will provide the visual confirmation the physician needs that registration was performed properly, and the system is ready to deliver the treatment pattern(s). Thus, while the system 10 locks registration in automatically once the physician aligns the delivery system 68 at or close to the intended targeted tissue, the registration should be visually confirmed by the physician before treatment begins.

Once registration is achieved, the overlaid visual display of the live image and the pre-treatment image may indicate to the physician that further manual alignment may be necessary to better center the delivery system alignment to the target tissue as defined by the treatment template. Misalignment may also be caused by movement of the patient's eye. Thus, there may be additional alignment of the delivery system 68 to the patient's eye by the physician both during and after the image registration of step 5. Alignment confirmation can be performed in several different ways. The physician can manipulate delivery system alignment until the target tissue defined by the treatment template is within view of the display showing the image overlay, within a particular area on the display, or even in the center of the display. Alternately, an aiming beam can be directed to the eye that visually illustrates the alignment of the delivery system, whereby the physician adjusts alignment until the aiming beam is within (or even centered with respect to) the treatment pattern defined by the treatment template. Or, an alignment pattern as described above with respect to FIG. 1 is projected onto the patient's eye, and the physician adjusts delivery system alignment until the alignment pattern partially or fully overlaps with, or is centered with respect to, or even is perfectly aligned on a spot by spot basis to, the treatment pattern as defined by the treatment template and displayed on the image overlay display.

After registration has been confirmed, and any additional alignment by the physician is completed so that the delivery system 68 is aligned at or near the proposed treatment area, the physician activates treatment in step 6 by triggering an input device/control 64 (e.g. a foot pedal, a finger switch, or any other equivalent trigger device), where the system 10 applies the treatment pattern to the patient's eye. While the system could rely solely on the physician's alignment (and simply be configured to prevent treatment if the alignment is or becomes too misaligned relative to the target tissue defined by the treatment template), it is preferable that the system 10 actively manipulate alignment before and during treatment to achieve and/or maintain alignment of the delivery system 68 to the target tissue. More specifically, when the physician triggers treatment, the system 10 confirms that delivery system 68 is accurately aimed at the intended targeted tissue (as defined by the treatment template). If it is not, the system 10 (via control electronics 22) will search for the area designated for treatment, and if found will adjust the alignment of the delivery system 68 until it is aligned to that intended target tissue (i.e. such that the treatment pattern will be projected onto the eye tissue at the same locations and dosages as defined by the treatment template). Moreover, as the treatment pattern is being applied to the eye tissue, the alignment of the delivery system 68 will be constantly adjusted as needed to compensate for any eye movement detected by the system (i.e. the system will track real-time movements of the eye and make appropriate corrections to the alignment of the delivery system 68). With this technique, the physician need only align the delivery system 68 close to the intended target tissue (course adjust), where the system 10 will automatically complete and verify the alignment (fine adjust) using the treatment template and then automatically apply the treatment pattern to the eye tissue.

The true precision of the above described technique is achieved by the physician creating a detailed template showing exactly where treatment should occur and at what dosages, coupled with a system that uses that template to achieve and maintain alignment while applying the predetermined dosages of therapeutic light to the target tissue. Precision is also achieved because it is the actual tissue that is being treated (as opposed to the pupil, iris, or another adjacent tissue) that is also being imaged for alignment and dosage control. Moreover, because the system can manipulate the delivery system alignment to track moving target tissue, longer exposure times can be used to better project or paint patterns or moving spots onto the target tissue for more uniform treatment.

There are other advantages and uses for the treatment templates described above. The treatment template from one treatment session can be stored, and used later during a subsequent treatment session as an accurate indicator of past treatment locations. For example, in a PRP fill-in re-treatment, the treatment template from an earlier treatment session can be used to define and target tissue locations in-between previous laser treatments. Generic treatment templates can also be generated for widespread use among many candidate patients. For example, ophthalmic experts can prepare treatment templates for specific studies or optimized specialized treatment. These generic treatment templates can be mapped to specific patient geometries with some modifications, where the generic aspect of the intended treatment is retained.

The search range within the pre-treatment image and treatment template, and/or the amount of fine adjust applied to the delivery system 68, is reduced by including the physician's course alignment adjustment first, especially if the physician continuously attempts to bring the target tissue into alignment while the system corrects for eye movement as well. The above described system and technique increase precision, safety, and efficiency while reducing the risk of RPE creep caused by thermal diffusion, thus allowing the physician to safely treat tissues closer to sensitive areas such as the foveal avascular zone, the macula, previous laser marks, etc.

There are many applications for the semi-automated treatment system and technique described above, including treatment of microaneurysms for diabetic macular edema (using small, bright red dots as the identifier in the image), diabetic retinopathy and vein occlusions, branch retinal vein occlusion (BRVO), central retinal vein occlusion (CRVO), diabetic macular edema, focal extra-foveal or peripapillary choroidal neovascular membranes (CNV), central serous retinopathy (CSR) leaks, retinal angiomatous proliferation (RAP) lesions, retinal breaks, teleangectasia, or feeder vessels (typically identified by ICG, high frame rate angiography).

Figure 5:
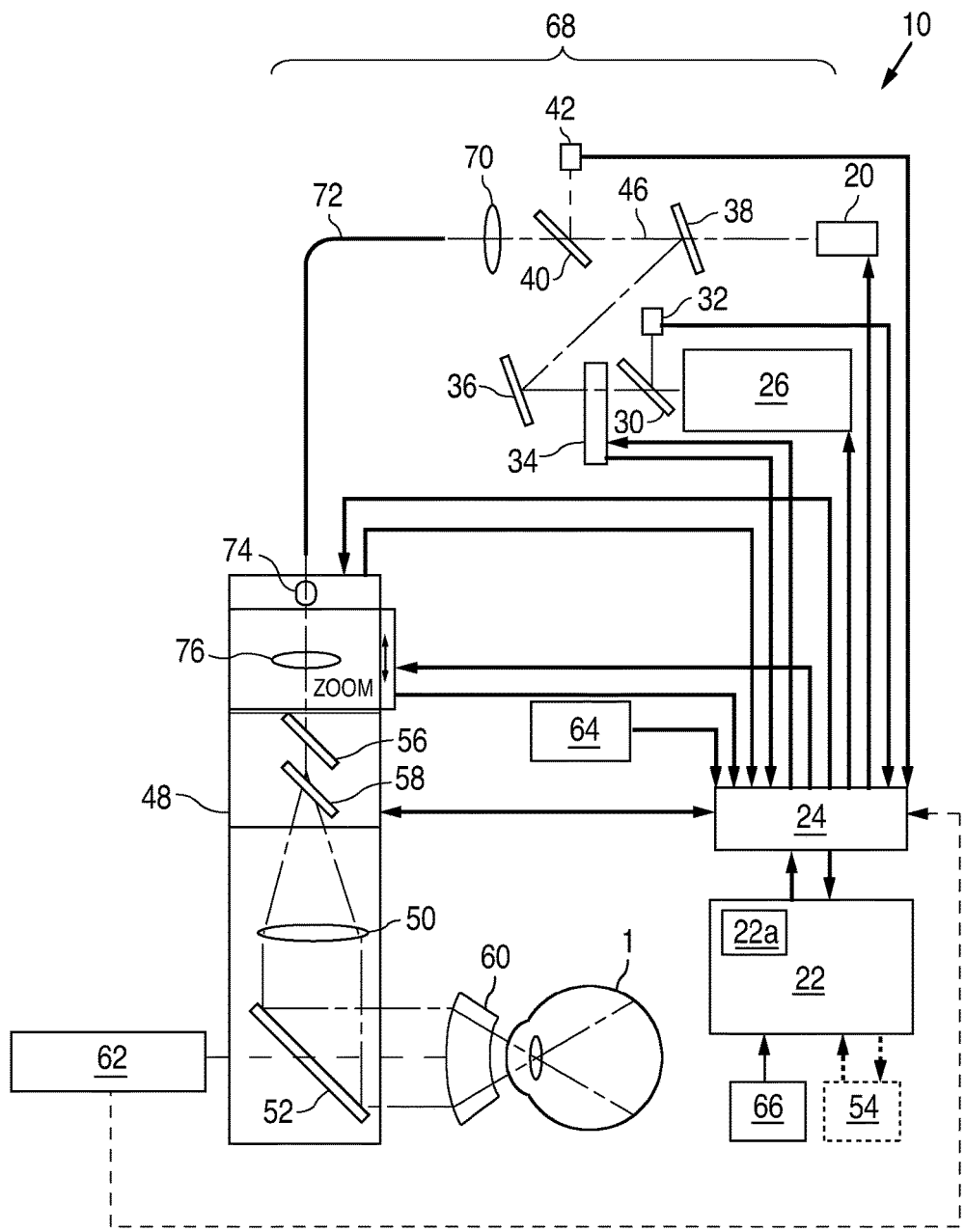
FIG. 5 is a schematic diagram illustrating an alternate embodiment of a light generation and scanner system for semi-automated ophthalmic treatment.

FIG. 5 shows a schematic diagram of an alternate embodiment to the system of FIG. 1, with optical fiber delivery. In this embodiment, lens 70 is used to inject the alignment and therapeutic light 46 into an optical fiber 72. Light 46 exiting optical fiber 72 encounters lenses 74 and 76 which condition the light and can act as a zoom system before the light enters the scanner assembly 48. An image of the output face of optical fiber 72 may be relayed to the target area, and a "flat-top" intensity profile used, rather than the Gaussian profile produced by gas lasers. The remainder of the system of FIG. 5 is the same as that shown in FIG. 1.

Figure 6:
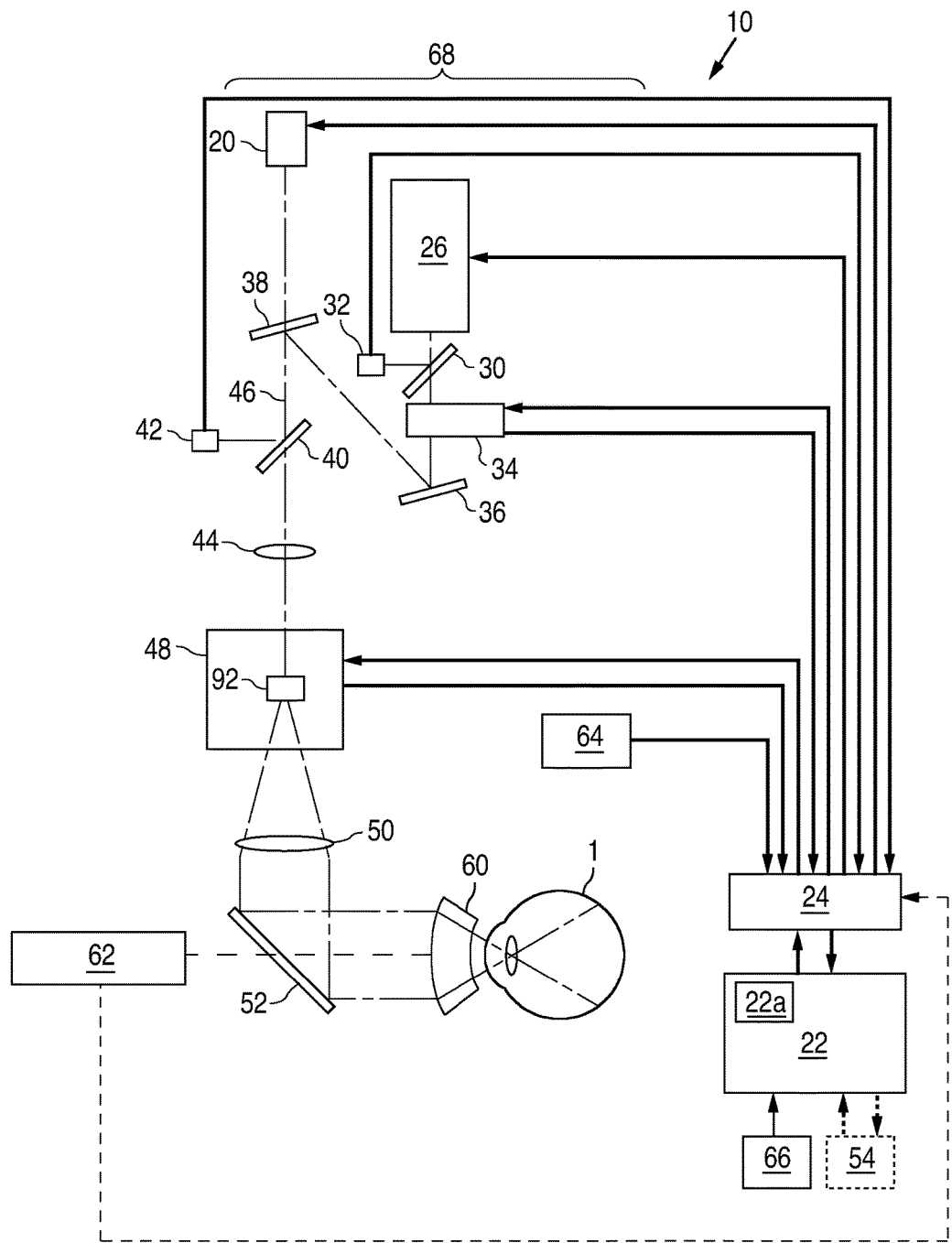
FIG. 6 is a schematic diagram illustrating a second alternate embodiment of a light generation and scanner system for semi-automated ophthalmic treatment.

FIG. 6 shows a schematic diagram of another embodiment which is similar to that discussed above with respect to FIG. 1, but with the addition of an adaptive optical element 92 in replacement of scanning mirrors 56/58 in scanning assembly 48, for scanning the light 46. In this embodiment, adaptive optical element 92 may be reconfigured to produce a complex optical system. For example, both a scan and any possible anamorphic correction maybe made to light 46 with this single element. Some examples of such an optical element 92 include: deformable mirrors, deformable lenses, and optical phase arrays. Scanner 48 could take other configurations as well. Specifically, for significant eye movement, the scanner 48 can incorporate additional optics for additional degrees of freedom, such as compensation for 5 degrees-of-freedom movement of a retinal target with respect to the delivery system (3-D translations, pitch, yaw). For example, if the eye rotates significantly upward, pitch compensation up may not be sufficient, whereas an optical system that can translate down and pitch up while moving in with focus can be more versatile (possibly with the aid of the physician). Other techniques of scanning light beam 46 could include the light sources as part of the scanner assembly 48 (i.e. beam movement by moving the light sources 20/34 themselves directly), just using a single moving optical element elsewhere in the delivery system (e.g. mirror 52), or manipulating any of the other optical elements in the delivery system 68. If optical elements 56/58 have optical power, then compensating optical elements (not shown) may be added to produce an image, as opposed to a simple illumination, on the target tissue.

It is to be understood that the present invention is not limited to the embodiment(s) described above and illustrated herein, but encompasses any and all variations falling within the scope of the appended claims. For example, while the scanner 48 is ideal for making the necessary (fine) alignment adjustments, other optical elements in the delivery optical chain can be moved or used to otherwise implement the fine position adjustment of the treatment pattern before it is applied. Additionally, while lasers are the preferred light sources for the treatment and/or alignment light, any appropriate light sources can be utilized. It should be noted that therapeutic light can be for diagnosis and/or treatment purposes. While scanning assembly is described as forming both an alignment pattern and a treatment pattern, it could simply pass along an aiming beam from the alignment light source to visually indicate a center or other position of the treatment pattern or a simple treatment beam. The functionality of the control electronics can be implemented entirely by one or more electrical components, and/or include one or more components or modules found in software and/or firmware.

What is claimed is:

1. An ophthalmic treatment system for performing therapy on target tissue in a patient's eye, comprising:
   a light source configured to produce treatment light;
   a delivery system configured to deliver the treatment light to the patient's eye;
   a storage device configured to store a pre-treatment image of the patient's eye;
   a camera configured to capture an image of the patient's eye; and
   a computer operatively connected to the light source, the delivery system, and the camera via at least one input/output device or input port associated with the computer, and comprises or is operatively connected to the storage device via at least one input/output device or input port associated with the computer, the computer being configured to:
      locate an area of the patient's eye that indicates a previous treatment, comprises a large vessel, or comprises blood;
      build a treatment pattern included in a treatment template that identifies the target tissue in the pre-treatment image such that the target tissue is not part of the located area;
      register the pre-treatment image and the treatment template to the captured image;
      set a position onto which the treatment light is projected in the patient's eye by using the treatment template;
      control the delivery system based on the set position so that the treatment light is projected onto the position; and
      control a dosage of light produced by the light source at the set position based on a dosage control information corresponding to a position within target tissue.

2. The ophthalmic treatment system of claim 1, wherein the computer is further configured to mark around the position onto which the treatment light is projected.

3. The ophthalmic treatment system of claim 1, wherein the computer is further configured to set a position onto which projection of the treatment light is to be avoided, and to control the delivery system so that the treatment light is not projected onto this position to be avoided.

4. The ophthalmic treatment system of claim 3, wherein the computer is further configured to mark around the position at which the projection of the treatment light is to be avoided.

5. The ophthalmic treatment system of claim 1, further comprising a display device that is used for displaying the image captured by the camera.

* * * * *